United States Patent [19]

Vali et al.

[11] Patent Number: 5,004,914
[45] Date of Patent: Apr. 2, 1991

[54] FIBER-OPTIC INTERFEROMETRIC CHEMICAL SENSOR

[75] Inventors: Victor Vali, Laguna Hills; David B. Chang, Tustin; Patrick C. Brownrigg, Long Beach, all of Calif.

[73] Assignee: Hughes Aircraft Company, Los Angeles, Calif.

[21] Appl. No.: 511,666

[22] Filed: Apr. 20, 1990

[51] Int. Cl.$^5$ ............................................. H01J 5/16
[52] U.S. Cl. .................................. 250/227.27; 356/345
[58] Field of Search ....................... 250/227.21, 227.27; 356/345

[56] References Cited

U.S. PATENT DOCUMENTS 4,678,904 7/1987 Saaski et al. ................. 250/227.27
4,818,064 4/1989 Youngquist et al. ........... 250/227.27

Primary Examiner—David C. Nelms
Assistant Examiner—Khaled Shami
Attorney, Agent, or Firm—Michael W. Sales; Wanda Denson-Low

[57] ABSTRACT

A fiber-optic interferometric chemical sensor for detecting chemical vapors in the air. The chemical sensor 10 includes a light source 12 which outputs an optical signal to a first beam splitter 14. The first beam splitter 14 splits the optical signal into first and second components and transfers the optical signal over sensor and reference optical fibers 20 and 22 respectively. The optical fibers 20 and 22 are bonded to the sensor and reference magnetostrictive substrates 24 and 26, which oscillate in response to an oscillating electromagnetic field generated by a coil 28 circumscribing the substrates 24 and 26. The sensor substrate 24 is further coated with a substance to facilitate collection thereon of molecules associated with the chemical vapor being detected. The optical outputs of the optical fibers bonded to the substrates 24 and 26 are then output to second and third beam splitters 16 and 18 respectively, and first and second beam combiners 32 and 34 respectively. The beam splitters 16 and 18 and beam combiners 32 and 34 operate cooperatively to provide an interferogram which is output to a signal processing circuit 44. The signal processing circuit provides an electrical signal indicative of the collection on sensor substrate 24 of molecules of the chemical vapor being detected, and outputs the signal to a display system 46.

15 Claims, 2 Drawing Sheets

FIBER-OPTIC INTERFEROMETRIC CHEMICAL SENSOR

BACKGROUND OF THE INVENTION

1. Technical Field

The present invention relates generally to chemical sensors and, more particularly to a fiber-optic interferometric chemical sensor employing a plurality of mechanical oscillators.

2. Discussion

Chemical detection devices are used in a wide variety of applications. In particular, such devices are especially useful in detecting the presence of narcotics and other illegal or controlled substances, as well as concealed explosives. With the significant increase in Federal spending aimed at interdicting illegal drug use and terroristic activities, more effective and efficient technological approaches for detecting drugs and explosives at areas such as airports, border checkpoints, etc., are needed.

One form of chemical detection device presently used for the above-mentioned purposes employs spectroscopic-based techniques. Basically, these devices sample the air by passing it through a filter having a surface coating adapted to adhere to the chemical vapors being detected. The filter traps molecules of the chemical vapor being detected and is then burned (i.e., vaporized) to produce a light spectrum indicative of the presence or absence of the chemical vapor being detected. A spectrometer is then employed to split the various wavelength components of the light spectrum due to the vaporization of the chemical vapor. The spectrometer produces a pattern of lines characteristic of the presence or absence of the chemical being detected.

Spectroscopic-based systems, however, are extremely costly as they require the use of a complex spectrometer for detecting the presence of the chemical molecules. In addition, spectrometers suitable for this purpose are large, relatively stationary, and somewhat delicate instruments that are not easily transported and require special training to operate properly and reliably.

Another type of chemical detection device presently used employs quartz crystals as mechanical oscillators. Such devices generally measure the change in frequency of an oscillating quartz crystal as it is affected by the mass of molecules which are being detected. The change in mass, however, of quartz crystal oscillators as they absorb chemical vapors, is so small that the change in their frequency of oscillation is also extremely small. This limits the sensitivity of quartz crystal-based detection devices and the number of different applications in which they can be reliably employed.

It is therefore a principal object of the present invention to provide a chemical sensing device which is capable of detecting minute chemical vapors associated with illegal or controlled chemical substances and explosives.

It is a further object of the present invention to provide a chemical detection device which is more sensitive than present day detection devices and is operable to detect more reliably even smaller traces of illegal chemical substances in the air.

It is still a further object of the present invention to provide a chemical detection device which poses no safety hazard to operators of the device, bystanders, or the environment.

It is a further object of the present invention to provide a chemical detection device which has no moving parts, is of a technologically simple construction, is reliable, and is easily maintainable and operable by relatively unskilled personnel.

It is another object of the present invention to provide a chemical detection device which is compact, low in weight, and relatively inexpensive.

SUMMARY OF THE INVENTION

The above and other objects are accomplished by a fiber-optic interferometric chemical sensor in accordance with the present invention. The chemical sensor generally comprises a sensor magnetostrictive substrate and an isolated reference magnetostrictive substrate. The sensor magnetostrictive substrate further includes collecting means thereon for collection of the chemical vapor being detected. The substrates are operable to change dimensions in an oscillating fashion in response to exposure to an oscillating magnetic field caused by a magnetic field generator. A sensor optical fiber is secured to the sensor substrate while a reference optical fiber is secured to the reference substrate. The optical fibers are operable to change optical path lengths in response to the oscillating dimensional changes of the substrates.

The chemical sensor of the present invention further includes a light source operable to provide an optical input signal to the sensor and reference optical fibers. The oscillating substrates cause the optical path lengths of each optical fiber to change, thereby producing oscillating optical sensor and reference signals having certain resonant frequencies. The resonant frequency value of the oscillating sensor optical signal is further responsive to the presence of the chemical vapor being detected.

The optical output of the reference and sensor signals are then input to a fiber-optic beamsplitter/beam combiner combination which generates an interferogram indicative of the presence of the chemical vapor. The interferogram is then output to a signal processing circuit which is operable to provide an indication to a user of the chemical sensor of the presence of the chemical vapor.

In a preferred embodiment of the Present invention, the collection means comprises an antibody coating specific to the particular chemical vapor being detected, which is applied to the sensor substrate to facilitate detection of the particular, desired chemical vapor.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
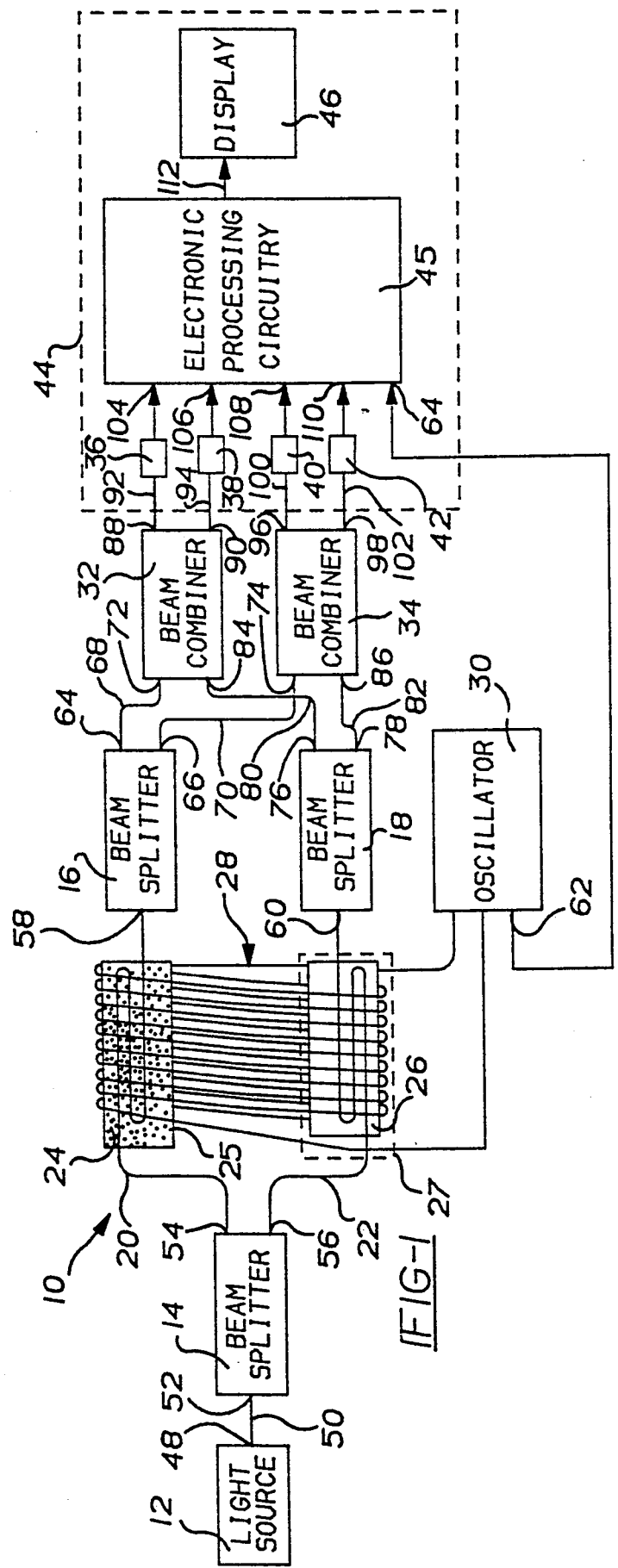
FIG. 1 is a simplified block diagram of a fiber-optic interferometric chemical sensor in accordance with the present invention.

Referring to FIG. 1, there is shown a fiber-optic interferometric chemical sensing system 10 in accordance with the present invention. The system 10 generally comprises a light source 12; first, second and third beam splitters 14, 16 and 18 respectively; sensor and reference optical fibers 20 and 22 respectively; sensor and reference magnetostrictive substrates 24 and 26 respectively; a coil 28; an oscillator 30; first and second beam combiners 32 and 34; photo-detectors 36–42; and signal processing circuitry 44 which includes electronic processing circuitry 45 and a display device 46.

The light source 12 has an output 48 which is coupled via an optical fiber 50 to an input 52 of first beam splitter 14. In a preferred embodiment of the present invention the light source 12 comprises a frequency stabilized laser which is relatively unaffected by ambient temperature changes. The first, second and third beam splitters 14, 16 and 18 are preferably directional couplers commercially available from the Newport Research Corporation, Newport, Calif., under Part No. F-506A.

The first beam splitter includes two outputs 54 and 56 which are coupled to inputs 58 and 60 of beam splitters 16 and 18 respectively. The first optical fiber 20 is further disposed over the surface of the sensor magnetostrictive substrate 24 in a preferably zig-zag pattern to increase the total length of the portion of the optical fiber 20 which is in contact with the substrate 24. The zig-zag pattern generally helps to improve the sensitivity of the system 10. The optical fiber 20 may be secured to the substrate 24 by a wide variety of commercially available glues or epoxies such as DURO® Super Glue, available from loctite Corporation, Cleveland, Ohio. Securing of the fiber 20 is generally accomplished by tacking the fiber 20 to the surface of the substrate 24 at several points along the length of the fiber 20 which is in contact with the substrate 24. The reference optical fiber 22 is further arranged over and secured against the second magnetostrictive substrate 26 in a similar fashion and coupled to an input 60 of second beam splitter 18.

Sensor magnetostrictive substrate 24 is further coated with a "collecting substance" 25 to facilitate collection on substrate 24 of the molecules of the chemical vapor being detected. In a preferred embodiment of the present invention this substance 25 comprises an antibody which is specific to the particular chemical vapor being detected. The antibody is a protein having a high molecular weight of about 150,000, and is commercially available from IRT, Inc., San Diego, Calif.

The sensor substrate 24 is exposed to the environment so that it may collect thereon molecules of the chemical vapor being detected. This function of the sensor magnetostrictive substrate 24 will be discussed in more detail in the following paragraphs. The reference magnetostrictive substrate 26 is preferably contained within a hermetically sealed enclosure 27 to isolate it from the chemical vapor being detected.

In a preferred embodiment of the present invention the sensor magnetostrictive substrate 24 has a length of preferably about 10 cm, a width preferably in the range of about 2–5 in., and a thickness preferably in the range of about 10–25 um. It is also preferred that one substrate 24 or 26 is about 1 cm shorter than the other, although there is no preference to which substrate 24 or 26 is longer. The difference in length between the substrates 24 and 26 enables them to have different resonant frequencies. The substrate 24 has a resonant frequency of preferably about 10 KHz. Substrate 26 has a resonant frequency of preferably about 11 KHz.

The substrates 24 and 26 are preferably mounted in a fashion which enables them to oscillate. One preferred method is to lay both substrates 24 and 26 on sections of foam. A second preferred method is to suspend the substrates 24 and 26 by their respective optical fibers 20 and 22. Both of these methods will enable the substrates to oscillate without dampening or enhancing their frequencies of oscillation. Accordingly, it should be appreciated that a wide variety of mounting arrangements may be employed provided such arrangements do not affect the frequencies of oscillation of the substrates 24 and 26.

With further reference to FIG. 1, both substrates 24 and 26 are circumscribed by the coil 28. The coil is a conventional current-carrying wire or other conductor-like material which is coupled to oscillator 30. The oscillator 30 further has a reference output 62 which is coupled to an input 64 of electronic processing circuitry 45. The oscillator may take the form of a sine-wave generator or any other conventional oscillator-like circuit operable to generate an alternating electrical current having a frequency preferably in the range of about 10 KHz to 30 KHz. The alternating electrical current is operable to cause the coil 28 to generate an AC magnetic field of preferably less than about 1 gauss, and preferably about $1 \times 10^{-4}$ gauss RMS. The oscillator 30 is further operable to provide a DC bias current to generate a DC bias magnetic field of preferably about 2 gauss to help improve the sensitivity of the substrates 24 and 26.

The first beam splitter 16 further includes outputs 64 and 66 which are coupled via optical fibers 68 and 70 to inputs 72 and 74 of the first and second beam combiners 32 and 34. Second beam splitter 18 includes first and second outputs 76 and 78 which are coupled via optical fibers 80 and 82 to second outputs 84 and 86 respectively of beam combiners 32 and 34.

The first beam combiner 32 includes first and second outputs 88 and 90 respectively which are coupled via optical fibers 92 and 94 to inputs of photo-detectors 36 and 38. The second beam combiner 34 similarly has two outputs 96 and 98 which are coupled via optical fibers 100 and 102 to photo-detectors 40 and 42 respectively. It is preferred that the optical fibers 20, 22, 50, 68, 70, 80, 82, 92, 94, 100 and 102 each comprise a single mode optical fiber with birefringence and that each have an outer diameter of preferably about 125 microns.

The photo-detectors 36–42 preferably comprise silicon photo-diodes, the outputs of which are electrically coupled to inputs 104–110 of the electronic processing circuitry 45. The electronic processing circuitry 45 generates a final output signal 112 which is electrically coupled to the display 46. In a preferred embodiment the display 46 comprises a highly sensitive frequency counter 46. Highly sensitive frequency counters suitable for use in the present invention are commercially available from a variety of companies such as the Hewlett-Packard Company of Palo Alto, Calif.

With further reference to FIG. 1, a general description of the overall system 10 will now be given. The light source 12 first transmits a coherent beam of light through optical fiber 50 into the first beam splitter 14. Beam splitter 14 splits the optical input signal into approximately equal first and second components and transmits the components through optical fibers 20 and 22. Optical fiber 20 transmits its associated optical signal to beam splitter 16 where the signal is further split into first and second components having approximately equal magnitudes. The remaining optical signal component is transmitted from output 56 through the second optical fiber 22 into third beam splitter 18 where the optical signal component is further split into first and second components having approximately equal magnitudes.

The first and second substrates 24 and 26 are preferably made from foils having magnetostrictive properties. The magnetostrictive properties of the foils enable the foils to change dimensions slightly when exposed to a magnetic field. In a preferred embodiment of the present invention the substrates 24 and 26 are comprised of independent strips of METGLAS ® foil, commercially available from the Allied Signal Corporation.

The oscillator 30 generates an alternating current at a frequency of preferably about 11 KHz, which is preferably about equal to the resonant frequency of the reference magnetostrictive substrate 26 and preferably within about 1 KHz of the resonant frequency of the sensor substrate 24. The alternating current causes an oscillating magnetic field to be generated in the coil 28, which excites the substrates 24 and 26 causing them to oscillate at frequencies in accordance with the frequency of the alternating current.

With further reference to FIG. 1, the frequency of oscillation of the sensor magnetostrictive substrate 24 will change slightly in response to the collection thereon of molecules of the chemical vapor being detected. This small frequency change is represented by the following formula: $f = c/\sqrt{m}$, where "f" represents the resonant frequency of sensor substrate 24, "m" represents its mass, and "c" is a constant that depends on the Youngs modulus and the geometry of the oscillator 30. Therefore, the change in frequency ($\Delta f/f$) of oscillation of sensor substrate 24 will be approximately equal to ($\Delta m/2m$). Thus, by measuring the shift in the resonant frequency of sensor substrate 24, the presence of molecules associated with the chemical vapor may be detected in the ambient environment surrounding the sensor substrate 24.

Since the optical fibers 20 and 22 are adhered to the substrates 24 and 26, the optical path lengths of the fibers 20 and 22 change in accordance with the magnitude of the oscillating magnetic field generated by oscillator 30 through the coil 28. This causes changes in the phases of the optical input signals transmitted through optical fibers 20 and 22. Since the reference substrate is not coated with an antibody and is environmentally isolated, its resonant frequency of oscillation will remain constant. Accordingly, third beam splitter 18 receives a relatively stable, oscillating reference optical signal at its input 60. Sensor substrate 24, however, because of its antibody coating 25 and its exposure to the environment, will change its resonant frequency of oscillation as molecules associated with the chemical vapor being detected are collected thereon. This causes the beat between the reference and sensor signals being transmitted through optical fibers 20 and 22 to change accordingly and generate an oscillating, optical, sensor signal of varying magnitude at outputs 88, 90, 96 and 98. The first optical fiber 20 and sensor magnetostrictive substrate 24 thus operate cooperatively to provide an oscillating, optical, sensor signal for indicating the presence of a specific chemical vapor in the air. The second optical fiber 22 and second magnetostrictive substrate 26 operate cooperatively to provide an oscillating, optical reference signal which when combined with the oscillating, optical, sensor signal at beam combiners 32 and 34, provides a varying frequency of oscillation indicative of the difference in resonant frequencies between the reference and sensor substrates 24 and 26.

The oscillating, optical, sensor signal is next divided by second beam splitter 16 into first and second components having magnitudes which are preferably about equal. These two components are then transmitted into the first inputs 72 and 74 of beam combiners 32 and 34 respectively. The third beam splitter 18 similarly splits the oscillating, optical reference signal into first and second components and transmits these components to the second inputs 84 and 86 of beam combiners 32 and 34. In a preferred embodiment of the present invention beam combiners 32 and 34 comprise fiber couplers commercially available from Canadian Instrumentation Ltd., Burlington, Ontario, Canada under Part No. 904P-P 50-50. The beam combiners 32 and 34 each operate to combine components of the oscillating, optical sensor and reference signals thus providing a beat frequency that is equal to the difference in frequency between the reference and sensor arms of the interferometer and to cause the components to interfere constructively and destructively to form optical fringe patterns at outputs 88, 90, 96 and 98. The brightness of the fringe patterns generated at each output 88, 90, 96 and 98 thus represents the relative optical path length (i.e., phase) of the optical signals transmitted through optical fibers 20 and 22 and into beam splitters 16 and 18. The fringe patterns at outputs 88, 90, 96 and 98 further provide a quadrature condition represented by their intensities. In practice, the fringe patterns at outputs 88 and 90 will be approximately 180° out of phase and would each appear as a dot of light of varying intensity if projected onto a flat plane. The fringe patterns at outputs 96 and 98 are similarly about 180° out of phase and would also appear as dots or points of light having varying intensities if projected onto a flat plane. The normalized fringe intensities I1, I2, I3 and I4 of the fringe patterns at outputs 88, 90, 96 and 98 respectively may be represented as a function of phase by the following formulas:

$$I_1 = 1 - \text{SIN } \Delta\phi$$
$$I_2 = 1 + \text{SIN } \Delta\phi$$
$$I_3 = 1 - \text{COS } \Delta\phi$$
$$I_4 = 1 + \text{COS } \Delta\phi$$

where ($\Delta\phi$) is the sum of the phase changes ($\Delta\phi_T$) caused by the collection of chemical vapor molecules on the sensor substrate 24 and the small phase changes induced by the oscillating magnetic field.

The beam combiners 32 and 34 thus act to provide a quadrature-like indication of the intensities of the optical output signals transmitted on optical fibers 92, 94, 100 and 102. Further details of the configuration of the beam combiners 32 and 34 are disclosed in a co-pending application assigned to the assignee of the present invention, entitled "Stable Passive Read-Out For Fiber-Optic Interferometer", U.S. application Ser. No. 341,009, filed 4/20/89.

Figure 2:
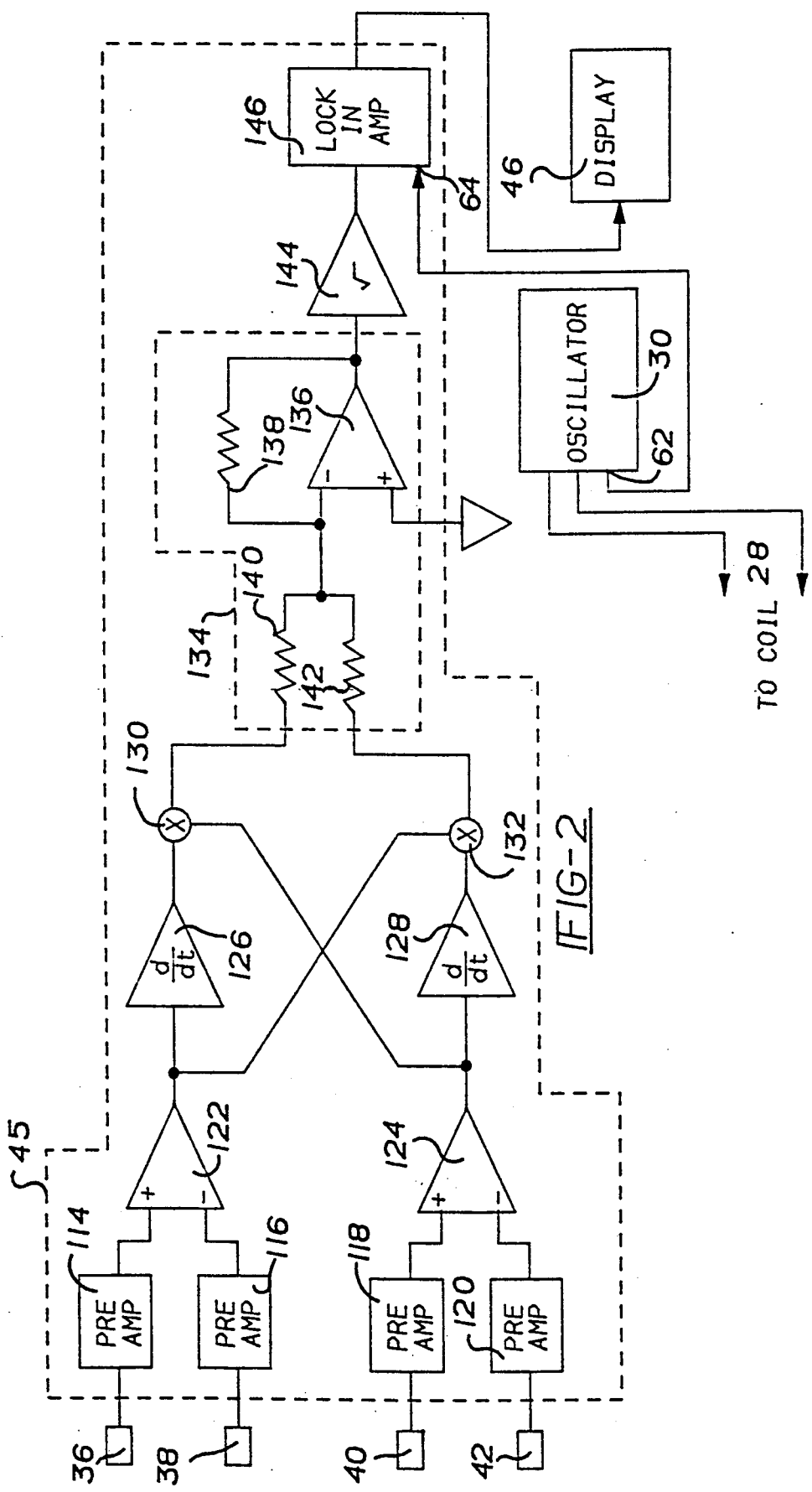
FIG. 2 is a simplified schematic diagram of the signal processing circuitry of the present invention.

Referring now to FIG. 2, a simplified schematic diagram of the signal processing circuitry 44 of the present invention is shown. Circuitry 45 generally includes the following components: pre-amplifiers 114, 116, 118 and 120; differential amplifiers 122 and 124; differentiators 126 and 128; product junctions 130 and 132; a summing amplifier 134 consisting of operational amplifier 136, feedback resistor 138, and summing resistors 140 and 142; a circuit 144 for obtaining the square root of a value represented by the output of summing amplifier amplifier 134; and a lock-in amplifier 146. Output 62 of oscillator 30 is also shown coupled to input 64 of lock-in amplifier 146.

In operation, the photo-detectors 36, 38, 40 and 42 transmit electrical signals of varying magnitudes into their respective pre-amps 114, 116, 118 and 120. Pre-amps 114 and 116 operate to amplify slightly the electrical signals they receive and to output the electrical signals into differential amplifier 122. Pre-amps 118 and 120 operate in a similar fashion to output their associated electrical signals into differential amplifier 124. Differential amplifier 122 operates to amplify the difference between the electrical signals received and to output an amplified first difference signal to differentiator 126 and product junction 132. Differential amplifier 122 operates similarly to output a second difference signal to differentiator 128 and product junction 130. Project junction 130 operates to take the product of the difference signal output from differential amplifier 124 and the output from differentiator 126. Product junction 132 likewise operates to take the product of the difference signal output by differential amplifier 122 and the output signal from differentiator 128. Product junctions 130 and 132 are preferably integrated circuit analog multipliers commercially available from Analog Devices, Inc., Norwood, Mass. under Part No. AD532.

In effect, the differential amplifiers 122 and 124, differentiators 126 and 128, and product junctions 130 operate cooperatively to determine the variations in the normalized fringe outputs, i.e , $(I_2-I_1)$ and $(I_4-I_3)$. More specifically, these variations may be represented by the following equations:

$$\delta(I_2-I_1) = 2 \sin \Delta\phi_T \delta\Delta\phi, \text{ and} \quad (131)$$

$$\delta(I_4-I_3) = 2 \cos \Delta\phi \delta\Delta\phi, \quad (133)$$

The outputs of product junctions 130 and 132 are electrically coupled to resistors 140 and 142 respectively of summing amplifier 134. Summing amplifier 134 operates to sum the electrical signals from product junctions 130 and 132 (i.e., the signals represented by equations 131 and 133) and to amplify the signals via operational amplifier 136. In a preferred embodiment of the present invention, op-amp 136 is configured via resistors 138, 140 and 142 to provide a gain preferably in the range of about 1–10.

The output of op-amp 136 is then input to electronic circuit 144 which takes the square root of the signals previously summed by summing amplifier 134. In effect this function may be represented by the following formula:

$$\sqrt{\delta(I_2-I_1)^2 + \delta(I_4-I_3)^2} = \delta\Delta\phi$$

In a preferred embodiment, the function of circuit 144 may also be performed by integrated circuit AD532 from Analog Devices, Inc. The output of circuit 144 is then input to the lock-in amplifier 146, which operates as a phase-sensitive detection device to detect phase changes in the electrical signal output from circuit 144. Lock-in amplifier 146 is also a commercially available item and may be obtained from Princeton Applied Research, Inc., Princeton, N.J., under Part No. 5301. The output from lock-in amplifier 146 represents an electrical signal whose magnitude varies when the sensor substrate 24 becomes exposed to the chemical vapor being detected. To provide a visual indication of this occurrence, the output from lock-in amplifier 146 is coupled to an input of the display 46 which, in a preferred embodiment of the present invention, comprises a commercially available frequency counter capable of monitoring small frequency changes down to $1 \times 10^{-4}$ Hz.

It should be appreciated that to reuse the system 10 after a desired chemical vapor has been detected, optical fiber 20 may incorporate a suitable detachable coupling device on each side of the sensor substrate 24. This allows the sensor substrate and its resident antibody coating to be detached and replaced after each detection. Alternatively, the used antibody coating could simply be removed and the substrate 24 re-coated with the desired antibody. In this manner, replacement of the substrate 24 would not be required.

The chemical sensing system 10 of the present invention thus acts as an ultra-sensitive vapor detector which has sufficient sensitivity to detect the presence of about $3 \times 10^{-12th}$ atmosphere. The system 10 further poses no hazards to bystanders or operators of the system and is reliable, easily maintainable, transportable and operable by relatively unskilled personnel. These features allow the system 10 to be used at airports, border checkpoints, etc., where it is desired to detect chemical vapors associated with illegal drugs, explosives, or other controlled substances.

Those skilled in the art can now appreciate from the foregoing description that the broad teachings of the present invention can be implemented in a variety of forms. Therefore, while this invention had been described in connection with a particular example thereof, the true scope of the invention should not be so limited since other modifications will become apparent to the skilled practitioner upon a study of the drawings, specification and following claims.

What is claimed is:

1. An apparatus for detecting presence of a given chemical vapor, said apparatus comprising:
   a light source;
   a first substrate exposed to the chemical vapor;
   collector means on the first substrate for collecting the chemical vapor onto the substrate;
   a first optical fiber on the first substrate and coupled to the light source;
   a second substrate isolated from the chemical vapor;
   a second optical fiber on the second substrate and coupled to the light source;
   magnetic field generator means for subjecting both first and second substrates to an oscillating magnetic field;
   said first and second substrates being constructed so that the dimensions thereof change in response to the oscillating magnetic field thereby altering characteristics of light from the light source passing through the first and second optical fibers, characteristics of the light in the first optical fiber being different from the characteristics of the light in the second optical fiber when the first substrate is exposed to said given chemical vapor whereby said first optical fiber provides an optical sensor signal and said second optical fiber generates an optical reference output signal; and
   means for comparing said optical sensor signal with said optical reference output signal and for providing an output signal, based on said comparing, which is indicative of the presence of said given chemical vapor.

2. The apparatus of claim 1, wherein said means for comparing said optical sensor signal with said optical reference signal and for providing an output signal indicative of the presence of said given chemical signal comprises:
  interferometer means responsive to said optical sensor and optical reference signals for generating an interferogram; and
  signal processing means responsive to said interferogram for indicating the presence of said chemical vapor.

3. The apparatus of claim 1, wherein said light source comprises a frequency stabilized laser.

4. The apparatus of claim 1, further comprising:
  a first beam splitter interposed between said light source and said first and second substrates, said beam splitter being operable to split said light from said light source and transmit approximately half of said light to said second optical fiber.

5. The apparatus of claim 1, wherein said magnetic field generator means comprises:
  a coil circumscribing said first and second substrates; and
  an oscillator circuit operable to supply an oscillating electrical signal to said coil to thereby generate said oscillating magnetic field.

6. The apparatus of claim 1, wherein said collector means comprises an antibody coating operable to facilitate the collection of said chemical vapor on said first substrate.

7. The apparatus of claim 2, wherein said interferometer means comprises:
  an input beam splitter coupled to an output of said light source and to said first optical fiber for splitting said light into first and second components having approximately equal magnitudes;
  a sensor beam splitter coupled to said first optical fiber, said sensor beam splitter being operable to split said optical sensor signal into first and second optical components having approximately equal magnitudes;
  a reference beam splitter coupled with said second optical fiber, said reference beam splitter being operable to receive said optical reference signal and to split said optical reference signal into first and second components having approximately equal magnitudes;
  a first beam combiner coupled to said outputs of said sensor and reference beam splitters, said first beam combiner being operable to cause said first components of said optical sensor and optical reference signals to combine and interfere to thereby form first and second fringe pattern output signals; and
  a second beam combiner operable to receive said second components of said optical sensor and optical reference signals and to combine said second components to thereby cause said second components to interfere, to thereby generate third and fourth fringe pattern output signals, whereby said first, second, third and fourth fringe pattern output signals operate cooperatively to provide said interferogram.

8. The apparatus of claim 2, wherein said signal processing means comprises:
  a plurality of photo-detectors for reading said interferogram and providing a plurality of photo-detector outputs indicative of said interferogram;
  a plurality of differential amplifier means responsive to said photo-detector outputs for determining differences between said photo-detector outputs and providing first and second differential outputs;
  differentiator means for determining the instantaneous rates of change of said photo-detector outputs and providing first and second differentiator output signals;
  first cross-coupling means for selectively taking the product of said second differential output and said second differentiator output signal;
  second cross-coupling means for selectively taking the product of one of said difference amplifier means and one of said differentiator means;
  summing amplifier means responsive to said first and second coupling means for summing said products of said first and second coupling means and providing an output signal indicative of the sum of said products;
  phase detection means responsive to said summing means for detecting differences in phase between said oscillating electrical signal and said output signal of said summing amplifier means and providing a phase detection output signal; and
  display means responsive to said phase detection output signal for providing an indication of a change in frequency of said first substrate.

9. An apparatus for detecting the presence of a chemical vapor in air, comprising:
  laser means for generating an optical input signal;
  oscillator means for generating an oscillating electrical signal;
  a coil coupled to said oscillator means for generating an oscillating magnetic field;
  first beam splitter means responsive to said optical input signal for generating first and second optical input signals;
  sensor substrate means disposed adjacent said coil for collecting thereon said chemical being detected, said sensor substrate means having a coating thereon specific to said chemical vapor being detected to facilitate collection thereon of said chemical vapor, said sensor substrate means further being operable to change dimensions in an oscillating fashion in response to said oscillating magnetic field generated by said oscillating means, said oscillating dimensional changes of said sensor substrate means further being responsive to the collection of said chemical vapor thereon;
  first optical fiber means secured to said sensor substrate means and coupled to said first beam splitter means and responsive to said oscillating dimensional changes of said sensor substrate means for providing an optical sensor signal indicative of the collection of said chemical vapor on said sensor substrate means;
  reference substrate means operable to change dimensions in response to said oscillating magnetic field for providing an oscillating reference signal;
  second optical fiber means coupled to said first beam splitter means and secured to said reference substrate means and responsive to said oscillating dimensional changes of said reference substrate means for generating an optical reference signal;
  second beam splitter means coupled to said first optical fiber means for receiving and splitting said optical sensor signal into first and second sensor output signals;

third beam splitter means coupled to said second optical fiber means for receiving and splitting said optical reference signal into first and second reference output signals;

first beam combiner means coupled to said second and third beam splitters for receiving and combining said first sensor output signal and said first reference output signal;

second beam combiner means coupled to said second and third beam splitter means for receiving and combining said second sensor output signal and said second reference output signal, said first and second beam combiner means operating to cooperatively generate an interferogram from said optical sensor and optical reference signals, said interferogram being operable to indicate the collection of said chemical vapor on said sensor substrate means; and signal processing means coupled to said first and second beam combiner means and responsive to said beam combiner output signals for generating a final output signal operable to provide an indication of the collection of said chemical vapor on said sensor substrate means.

10. The apparatus of claim 9, wherein said laser means comprises a frequency-stabilized laser.

11. The apparatus of claim 9, wherein:

said sensor and reference substrate means each comprise a magnetostrictive foil;

wherein said first optical fiber means is bonded to a surface of said sensor substrate means and said second optical fiber means is bonded to a surface of said reference substrate means; and wherein said first and second optical fiber means each have an optical path length which increases and decreases in accordance with a frequencY of said oscillating electrical signal.

12. The apparatus of claim 11, wherein:

said sensor substrate means has a resonant frequency;

wherein said frequency of said electrical oscillating signal is approximately equal to said resonant frequency of said sensor substrate means; and wherein said resonant frequency is within approximately 1 KHz of said resonant frequency of said reference substrate means.

13. A method for detecting the presence of a chemical vapor in air, comprising:

providing a first optical fiber secured to a first magnetostrictive substrate, said substrate being coated with a material specific to said chemical vapor;

providing a second optical fiber secured to a second magnetostrictive substrate;

providing an oscillating magnetic field to cause said first and second magnetostrictive substrates to oscillate at a first frequency;

providing an optical input signal to said first and second optical fibers;

exposing said first magnetostrictive substrate to said air for collection of said chemical vapor whereby said first magnetostrictive substrate will be caused to oscillate at a second frequency; and processing the optical signal output by said first optical fiber together with the optical signal output by said second optical fiber to generate a signal indicating the presence of said chemical vapor.

14. A chemical detection apparatus for detecting the presence of a chemical vapor in air, comprising:

laser means for generating an optical input signal;

oscillating means for generating an oscillating electrical signal;

a coil responsive to said oscillating means for generating an oscillating magnetic field;

sensor substrate means disposed within said magnetic field for collecting thereon said chemical vapor being detected, said sensor substrate means further being operable to change dimensions at a first frequency in response to said oscillating electrical signal, said first frequency further being responsive to the collection of said chemical vapor on said sensor substrate means;

optical sensor fiber means secured to said sensor substrate means and responsive to said optical input signal and said oscillating dimensional changes of said sensor substrate means for providing an optical sensor output signal relating to said oscillating dimensional changes of said sensor substrate means and indicative of a variation in said first frequency, said variation of said first frequency being operable to indicate the collection of said chemical vapor on said sensor substrate means;

reference substrate means operable to change dimensions in response to said oscillating magnetic field for providing an oscillating reference signal in accordance with said oscillating magnetic field;

optical reference fiber means secured to said reference substrate means and responsive to said optical input signal and said oscillating dimensional changes of said reference substrate means for generating an oscillating optical reference output signal;

interferometer means responsive to said oscillating optical sensor and optical reference output signals for generating an interferogram indicative of a in frequency between said oscillating optical sensor and optical reference output signals; and signal processing means responsive to said interferogram and said oscillating means for generating a final output signal indicative of said change in frequency between said oscillating optical sensor and optical reference output signals, said change in frequency being indicative of the collection of said chemical vapor on said sensor substrate means.

15. The apparatus of claim 14, wherein said first magnetostrictive substrate comprises an antibody coating thereon operable to facilitate collection on said said first magnetostrictive substrate of said chemical vapor being detected.

* * * * *